United States Patent [19]

Viza et al.

[11] 4,224,404

[45] Sep. 23, 1980

[54] PRODUCTION OF SPECIFIC IMMUNE NUCLEIC ACIDS CELL DIALYSATES AND ANTIBODIES

[75] Inventors: Dimitri Viza, Bourg-la-Reine, France; Dimitri Adamopoulos, Athens, Greece; John Phillips, L'Hay les Romes, France

[73] Assignee: The International Institute of Differentiation Limited, Guernsey, Channel Islands

[21] Appl. No.: 860,451

[22] Filed: Dec. 14, 1977

[30] Foreign Application Priority Data

Dec. 16, 1976 [GB] United Kingdom ............... 52674/76

[51] Int. Cl.² .............................................. A01N 1/02
[52] U.S. Cl. ....................................................... 435/2
[58] Field of Search .............................. 195/1.8; 435/2

[56] References Cited

FOREIGN PATENT DOCUMENTS

1229888 4/1971 United Kingdom .
1443948 7/1976 United Kingdom .

OTHER PUBLICATIONS

Moore et al.-J.A.M.A. vol. 199, No. 8, Feb. 20, 1967, pp. 87-92.
Baumal et al.-Nature vol. 230, 1971, pp. 20 & 21.
Nilsson et al.-Int. J. Cancer vol. 8, (1971), pp. 443-450.
Paltrowitz et al.-Mt. Sinai J. vol. 38, (1971), pp. 284-292.
Willmer—Cells and Tissues in Culture, (1966), vol. 3, pp. 330-334.

*Primary Examiner*—Frederick E. Waddell
*Attorney, Agent, or Firm*—Stevens, Davis, Miller & Mosher

[57] ABSTRACT

Gamma-globulins and immune nucleic acids, both specific to a given antigen, are produced by culturing in vitro an inducible cell line in the presence of specific immune nucleic acids or specific immune dialysates obtained either from human or animal donor lymphoid cells sensitized to said specific antigen or from cells of a previously induced cell line sensitized to said specific antigen, or in the presence of the liquid phase of a culture of a previously induced cell line sensitized to said specific antigen; and extracting gamma-globulins from the liquid phase of the thus induced cell culture and/or extracting the immune nucleic acids from the cells so cultured. Specific immune dialysates may also be produced by a similar process.

19 Claims, No Drawings

PRODUCTION OF SPECIFIC IMMUNE NUCLEIC ACIDS CELL DIALYSATES AND ANTIBODIES

This invention relates to the production of immunological material, and in particular concerns the production of gamma-globulins, immune nucleic acids and immune dialysates by the induction and cultivation of cell lines in vitro.

A fundamental necessity for the survival of animals is the ability to resist infection by parasitic organisms such as viruses, bacteria, fungi and parasitic animals constantly present in the environment. The immunity of animals to such organisms is provided by a variety of different mechanisms including phagocytosis, the chemical activity of antibodies, and the production of interferons to inhibit virus replication.

During the past two decades, there has been considerable research into various immunological fields, including the study of immune reactions involving the production of material which will specifically combat particular antigens introduced into an animal. The production of material capable of transferring these specific immune reactions either to unimmunised hosts when injected in vivo or to "naive" cells capable of immune reaction when incubated in vitro, is obviously of importance for medical and veterinary research. See, for example, H. S. Lawrence: "The transfer in humans of delayed skin sensitivity to streptococcal M substance and to tuberculin with disrupted leukocytes". J. Clin-Invest, (1955), 34, 219–30 or "Transfer of immunological information in humans with dialysates of leukocyte extracts". Trans. As. Amer. Physicians, (1968), 76, 84–91. The presence of living cells is essential for the replication of such immunological materials.

Lymphoid cells of animals which have been immunised against a specific antigen probably incorporate the immune information within their nucleic acids to form so-called "immune nucleic acids" which probably carry the immunological memory. Thus immune nucleic acids are characterised by their ability to confer immune reactivity against specific antigens to "naive" lymphocytes when injected in vivo, or when "naive" lymphocytes are incubated with the immune nucleic acids in vitro. Animals with such "sensitized" lymphoid cells can readily react on a new encounter with the corresponding antigen and resist, for instance, attacks from bacterial or viral organisms carrying this antigen.

A variety of in vitro cell lines of human and animal origin have been established, but no satisfactory culture system has emerged for the in vitro production of gamma-globulins, specific to a given antigen. Lymphoblastoid cells in culture may spontaneously produce antibodies which are directed to unknown antigens and they cannot thus be used for any practical purposes. Additionally, cells in culture frequently change their characteristics when cultivated for any length of time and lose some attributes of their differentiated state. It was therefore considered unlikely that a cell line could be found which was capable of being induced to produce specific immune nucleic acids; i.e. capable of incorporating within the cell's nucleic acids the information contained in the exogenous specific immune nucleic acids and, further, of replicating such specific immune nucleic acids. The production of specific antibodies (gamma-globulins) using a cell line culture was also thought improbable.

However, whilst carrying out research on an established lymphoblastoid cell line known as LDV/7, it was surprisingly discovered that when LDV/7 cells were incubated with specific immune nucleic acids (referred to hereinafter as i-RNA and i-DNA) obtained from donor, human or animal, lymphoid cells previously sensitized to a given antigen, the cells would incorporate this immunological information and would replicate the inducing molecules. Furthermore, when the induced LDV/7 cells were disrupted and subsequently dialysed, the dialysate was found to transfer specific cell-mediated immunity to other cells both in vivo and in vitro. Indeed, this immunity could be transferred to "naive" LDV/7 cells which would then continue to replicate the immune nucleic acids originally used. A dialysate with these properties is hereinafter referred to as immune-dialysate. It was also discovered that incubation of the cell line with immune nucleic acids and/or immune dialysates would induce the cells to produce gamma-globulins specific to the antigen against which the original donor had been immunised.

The LDV/7 cell line was developed from peripheral blood leucocytes obtained from a 75 year old, apparently healthy, male volunteer.

The cells can be grown in suspension culture, either in static cultures or spinner cultures and they can also be cultivated in agar. This property is particularly useful since it enables well established bacteriological methods to be applied to the in vitro control of human cells. Cloning is possible, for example, and it is also possible to study the effect of various factors, such as colony stimulating factor, on the differentiation of the cells.

The cell line was initially established by the following procedure (the percentages referred to throughout the Specification being by volume):

Most of the erythrocytes were separated from the original blood sample by the addition of 20% Plasmagel, and discarded after sedimentation in test tubes. The recovered suspension contained a ratio of erythrocytes to leucocytes of less than 20:1. The leucocytes thus recovered were then suspended in RPMI 1640 medium containing 20% foetal calf serum, at a concentration of $2 \times 10^6$ leucocytes/ml. Two thirds of the medium was replaced by fresh medium twice a week. Since cell death occurred within the first weeks, the cultures were concentrated as required in order to keep the cell concentration above $10^6$ cells/ml.

The cells were cultured in glass Roux bottles. Six weeks after the start of the cultures the cells in one of these bottles showed growth characteristics, i.e. they became larger and started multiplying and these were used to initially set up the LDV/7 cell line.

This cell line has since been grown in large quantities, using the propagation techniques described below:

The LDV/7 cell line can be maintained in a variety of nutrient media. It can be cultivated in RPMI 1640 medium containing from 5% to 30% foetal calf serum. Preferably, the nutrient medium consists of RPMI medium containing 10% foetal calf serum. Additionally, McCoy's and Eagle's Essential Medium may be used in subculturing the cell line.

The cells grow in suspension at 37° C., and form clumps which can be dispersed by gentle agitation of the medium. The cells are passaged at least three times a week. The usual seeding number is $5 \times 10^5$ cells/ml and the cells are allowed to grow in static culture until a concentration of $10^6$ cells/ml is reached. The cells will also grow in spinner culture in which a rotating, sterile magnetic stirrer keeps the cells in suspension in the nutrient medium. A higher concentration of the order of $1.5 \times 10^6$ cells/ml can then be obtained. The percentage of dead cells is roughly of the order of 5%, but varies according to culture conditions. The generation time of the cells is approximately 24 hours, again depending on the culture conditions.

In general, the conditions such as pH and temperature under which the cell line is propagated are substantially the same as those which leucocytes would encounter in a human being.

Karyotype analysis of the cells showed that the LDV/7 cell line is hypotetraploid. The number of chromosomes varies between 80 and 93. A study of the morphology of the cells under the light microscope revealed a heterogeneous cell size and that most of the cells have a blast-like appearance. Further work using an electron microscope confirmed the heterogeneity of the cell line, showing round mononuclear cells of varying size with cytoplasmic differentiation and rough endoplasmic reticulum, and macrophagic properties. There appears to be at least two cell populations, one of small cells of less then 15 μm diameters and one of large cells of from 15–30 μm diameters. Apparently the large cells derive from the small ones.

Three clones have been obtained with chromosome numbers of 84 for the first and 85 for the second and third, thus attesting cloning efficiency.

The phagocytic properties of the cells were also studied under the electron microscope. Some of the cells could clearly be seen to be phagocytised by other cells. No viral particles were discovered in the electron micrographs obtained, either from samples taken under the usual culture conditions or from cultures grown at +40° C. It is worth noting that this cell line is very sensitive to the adrenal cortical steroid hormone cortisone, suggesting the presence of lymphoblastoid cells and/or stem cells. It is also worth noting that no EB virus antigens were detected by immunofluorescence.

Tissue typing of the LDV/7 cells for histocompatibility HL-A antigens revealed the presence of the following specificities: HLA 2 and HLA 32 for the first locus, and HLA specificity W 14 for the second locus. However, weak reactivity with other antisera for other HLA specificities was also observed, but this was considered non-specific.

LDV/7 cells have been deposited at the Laboratoire d'Immunobiologie, Faculte de Medicine Broussais Hotel-Dieu, 15, rue de l'ecole de Medecine, Paris 75006, and are available to the public on request. The LDV/7 cell line and a process for its propagation is described and claimed in our co-pending Application Ser. No. 860,439 filed on even date herewith.

It is not possible in all cases to produce immunological material from other established cell lines, since not all cell lines are inducible in the manner described above in connection with the LDV/7 cell line. In particular, it was discovered that three lymphoblastoid cell lines obtained from leukaemia patients, two from Burkitt lymphoma tumors and three established from peripheral blood lymphocytes obtained from healthy volunteers could not be induced. However, successful induction was achieved when the lymphoblastoid cell lines BRI 8 and BEC 11 were employed, though not to the extent achieved for the LDV/7 cell line.

It has become apparent that a condition which must be met by a cell line for successful induction in a simple manner, and for that cell line to subsequently produce specific gamma-globulins, is the use of a cell line which is already producing gamma-globulins. Such gamma-globulins will, of course, be directed against unknown antigens, as noted previously. For example, cell lines of lymphoid origin (myeloma or lymphoblastoid cell lines) satisfying this criterion may be induced to produce specific gamma-globulins, i-RNA and i-DNA. However, the possibility that cell lines which do not spontaneously produce gamma-globulins may be induced should not be excluded. Induction of cell lines already producing gamma-globulins spontaneously, using the techniques described earlier in connection with the LDV/7 cell line, will thus lead to the production of gamma-globulins with the same specificity as the inducing material.

The present invention therefore provides a process for the production of gamma-globulins and immune nucleic acids (as hereinbefore defined), both specific to a given antigen which comprises:

(i) culturing in vitro an inducible cell line in the presence of specific immune nucleic acids or specific immune dialysates obtained either from human or animal donor lymphoid cells sensitized to said specific antigen or from cells of a previously induced cell line sensitized to said specific antigen, or in the presence of the liquid phase of a culture of a previously induced cell line sensitized to said specific antigen; and (ii) extracting gamma-globulins from the liquid phase of the thus induced cell culture and/or extracting the immune nucleic acids from the cells so cultured.

In a second aspect, the present invention provides a process for the production of immune dialysates, as hereinbefore defined, which comprises:

(i) culturing in vitro an inducible cell line in the presence of specific immune nucleic acids obtained either from human or animal donor lymphoid cells sensitized to said specific antigen or from cells of a previously induced cell line sensitized to said specific antigen, or in the presence of the liquid phase of a culture of a previously induced cell line sensitized to said specific antigen; and (ii) obtaining the immune dialysate from the cells so cultured.

In order to bring about the induction of certain cell lines, the conditions employed in connection with the LDV/7 cell line are sufficient. In other cases, trivial modifications of such techniques may be required, such as the time of incubation, or more subtle alterations may be necessary, such as changing the cell surface by the use of proteolytic enzymes or treatment with embryonic nucleic acids.

The cell lines which may be employed in the processes of the present invention include mutant cell lines derived from the LDV/7 cell line. Such a mutant cell line must of course be stable to be of any practical use. The heritable change causing the mutant cell line may be spontaneous, or may be induced by various chemicals or by physical agents such as X-rays or ultra-violet light.

In the process of the present invention for the production of specific gamma-globulins, it is preferred to culture cell lines of lymphoid origin (myeloma or lymphoblastoid cell lines) which spontaneously, before induction, produce gamma-globulins, for example, against unknown antigens in their culture media. More particularly preferred are myeloma cell lines. If a lymphoblastoid cell line is to be employed, it is particularly preferred to culture the LDV/7 cell line.

In both the production of immune nucleic acids, particularly i-RNA, and immune dialysates according to the present invention, inducible cell lines of lymphoid origin, as above, which spontaneously produce specific gamma-globulins before induction, may be employed. The use of the LDV/7 lymphoblastoid cell line is again preferred. These cell lines may of course also be used in the formation of immune dialysates by the process described above.

The immune nucleic acid or, in the process for the preparation of specific gamma-globulins or immune nucleic acids, immune dialysate used to initially induce the cell line employed is obtained from a previously immunised human or animal (for example, sheep, rabbit, guinea pig or rat) donor. When animal donors are employed, using germ-free animals immunised against one antigen, virtually monospecific sensitization is possible. The i-RNA may be extracted from the donor's lymphoid cells by the hot phenol method, and i-DNA by cold phenol extraction using a strong chelating agent, for example sodium 4-animosalicylate, and a detergent, for example sodium triisopropylnaphthalene sulphonate. Incubation of these immune nucleic acids or immune dialysates with an inducible cell line capable of replicating the inducing molecules, for example the lymphoblastoid cell lines known as LDV/7 and BRI 8, results in the production of large amonts of immune nucleic acids specific to a given antigen. The replication of the inducing immune nucleic acids takes place in the cell culture system at the same time as the replication of the cell's own nucleic acids during the normal course of cell division. It thus might be due to the derepression of endogenous nucleic acids, i.e. derepression of i-RNA. It should, however, be appreciated that there does not appear to be a species barrier preventing, for example, the induction of the lymphoblastoid cell line LDV/7, which is of human origin, by i-RNA obtaned from the lymphoid cells of sheep.

An immune-dialysate can subsequently be produced by disrupting the induced cells, for example, by repeated freeze-thawing techniques or by means of a homogeniser, and subsequently dialysing the homogenate. This immune-dialysate from human or animal leucocytes sensitized to a given antigen contain molecules of molecular weight less than 10,000. The dialysate is capable of transferring the immunological information to the cells in culture. These cells, after incubation with the inducing immune-dialysate, were found to produce i-RNA and i-DNA carrying the same specificity as the immune-dialysate used for induction. The activity of the immune-dialysate was not destroyed by treatment with RNAase or DNAase, but was destroyed by treatment with pornase. This would suggest that the information was carried by a small protein of molecular weight less than 10,000; and that this information could be transcribed into a nucleic acid. Although the mechanism of such transcription remains obscure, this result, namely the transfer of information from proteins to nucleic acids, is totally unexpected within the existing knowledge of molecular biology. It is worth noting that recent evidence suggests that the i-RNA responsible for transfer of the immunity to a specific antigen is messenger RNA: see P. Bibello, M. Fishman and G. Koch, Cell Immunol, 23, 309-319 (1976).

Specific antibodies (gamma-globulins) have been found in the liquid phase obtained from cultures of cells induced with i-RNA, i-DNA and/or immune dialysates. Suprisingly, these specific gamma-globulins (mainly IgG) were always of human specificity when the cell line employed was of human origin, even when the inducing immune nucleic acid was of animal origin (e.g. sheep, rabbit). This suggests again the derepression of the host cell genome by the animal nucleic acid. This is supported by the following evidence. The process of the induction of cell lines causes cell surface changes, and in particular the appearance of specific antigen receptors which are probably gamma-globulins. Further, experiments employing LDV/7 cells, sheep i-RNA and rabbit anti-sheep gamma-globulin show that no sheep gamma-globulins are dectable in the induced cultures, indicating that the specific gamma-globulins produced by the LDV/7 cells are human allotypes. Furthermore, when the specific antibodies were extracted on an immuno-adsorbent column for the corresponding antigen, and were tested after elution, only human allotypes were present.

Furthermore, the incubation of uninduced cells with the liquid phase from an induced culture does induce i-DNA and i-RNA production in the "naive" cells and also quite often the production of specific gamma-globulins. Consequently the inducing factors of the tissue culture medium as well as the antibodies can be extracted and purified. The gamma-globulins can be extracted using a specific immuno-adsorbent column with the corresponding antigen or xenogeneic antihuman globulin antibody on which the specific gamma-globulin contained in the medium would attach. The gamma-globulins can then be easily obtained by subsequent elution.

Although the Examples which follow are primarily concerned with the use of Key-hole limpet haemocyanin (KLH) as the sensitizing antigen, this is only because it has been found to be convenient experimentally to do so and in no way is to be taken to be a limitation of the generality of the sensitizing antigen which may be employed. Other antigens such as brucella bacteria, coccidioidin or histoplasmin have also been successfully used.

The use of the immunological materials hereinbefore described to transfer cell mediated immunity against specific antigens is of obvious importance in the field of medicine. The inducing molecules may be obtained, for example, from germ-free animals immunised against one antigen, thus obtaining vitually monospecific immune mediators. Cloning the cell cultures after induction will also result in a culture for the production of monospecific gamma-globulins. The bulk production of such mediators in vitro has wide applications. The use of immune dialysates presents an advantage over immune nucleic acids since it is barely possible to obtain immune reactions against the immune dialysates, and this avoids anaphylactic reactions. Furthermore, no viral hazard is possible using cell dialysates, whereas the hypothetical presence of a viral genome in immune nucleic acids will be cumbersome to exclude. Consequently a medicament capable of being administered in unit dosage, comprising at least one of the immune nucleic acids (i-RNA or i-DNA) and/or immune dialysates specific to a given antigen produced by a process as hereinbefore described is also within the scope of this invention. Specific human gamma-globulins produced in vitro should have a wide range of applications and can be used as substitutes for gamma-globulins obtained from animal or human donors and currently used in passive immonotherapy or for diagnostic purposes. Thus the invention also provides a medicament capable of being administered in unit dosage form comprising specific gamma-globulins produced by the process of the present invention.

The invention is further illustrated by the following Examples:

EXAMPLE 1

(a) General method of initial induction of cell line by immune nucleic acids obtained from a previously immunised donor.

An RNA-solution or DNA-solution obtained from the lymphoid cells of a donor previously immunised against a specific antigen were treated with DNAase and RNAase respectively to ensure that there was no DNA or RNA, again respectively, present. $10^7$ LDV/7 cells were incubated for 30 to 60 minutes with 0.5 to 1.00 mg of the RNA or DNA in solution.

The cells were suspended at a concentration of $5 \times 10^5$ cells/ml in RMPI 1640 medium complemented with 10% foetal calf serum. The culture was allowed to grow until the cells reached a concentration of $10^6$ cells/ml, and were then passaged in fresh medium which lowered the cell concentration to $5 \times 10^5$ cells/ml. The cells were harvested when the total yield of the culture was of the order of $10^{10}$ cells. Immune-RNA and immune dialysates were then obtained from these cells, and specific gamma-globulins were extracted from the tissue culture medium.

(b) General method of induction of cell line using dialysate obtained from initially induced LDV/7 cells. Dialysates of the cells prepared as above were obtained after freeze-thawing $10^9$ cells in 10 ml of distilled water and subsequent dialysis through a dialysis bag under vacuum.

100 ml of LDV/7 cells at a concentration of $5 \times 10^5$ cells/ml were incubated with the dialysates obtained from $5 \times 10^7$ cells induced as above. The cells were subcultured until the total yield was $2 \times 10^9$ cells and i-RNA, i-DNA and immune dialysates were obtained from the latter.

The specificity of the i-RNA obtained from the culture cells after induction with i-RNA, i-DNA or immune dialysate for malignant melanoma antigens was assessed in a cell-mediated cytotoxicity system. Malignant melanoma cell lines were the target cells. The cytotoxicity indices showed that immune nucleic acids or immune dialysates render "naive" inactive peripheral blood lymphocytes specifically cytotoxic to the target cells after incubation.

EXAMPLE 2

In a different series of experiments it was found that incubation of LDV/7 or BRI 8 cells with immune nucleic acids or immune dialysates as in Example 1 induces the appearance of specific antigen receptor sites on the cell surface of the lymphoblastoid cells.

(a) When LDV/7 cells were incubated with i-nucleic acids or immune dialysates specific for KLH (Keyhole-limpet haemocyanin), the LDV/7 cells subsequently developed receptor sites for this antigen. This can be seen by a rosette formation of SRBC (sheep red blood cells) which have been previously coated with KLH. Furthermore, in these experiments, specific anti-KLH antibody production could be detected in the culture medium.

(b) The lymphoblastoid cell line BRI 8 was induced employing the techniques of Example 1, in the presence of i-RNA and, in a second experiment, immune dialysates, both of which were specific for KLH. Subsequently, rosette formation was observed as in (a).

EXAMPLE 3

I-RNA used in this series of experiments was extracted from the lymph nodes and spleens of sheep immunized with either melanoma or colon carcinoma cells. Sheep immune RNA is hereinafter referred to as Is-RNA. I-RNA from a sheep immunized with Keyhole Limpet Haemocyanin (KLH) was used as a control.

The schedule for immunization of the sheep and the hot phenol method of extracting i-RNA have been described elsewhere: see D. H. Kern, D. Fritze, C. R. Drogemuller and Y. H. Pilch, J. Nat. Cancer. Inst. 57, 97–103 (1976), and L. L. Veltman, D. H. Kern and Y. H. Pilch, Cell. Immunol. 131, 367–377 (1974), respectively. The i-RNA preparations are assayed for their protein, DNA and RNA content. The sucrose density gradient profiles of the i-RNA are also determined, since these allow the estimation of any degradation destroying biological activity: see Y. H. Pilch, K. P. Ramming and P. J. Deckers. In H. Bush, Ed: Methods in Cancer Research, Vol 9, New York, Academic Press, 1973, 195–254.

The biological activity of these i-RNAs is assayed in an in vitro micro-cytotoxicity assay: see RNA in the Immune Response, H. Friedman, Ed, Ann, N.Y. Acad. Sci., 207, (1973). Their ability to convert normal allogeneic human peripheral blood lymphocytes to cytotoxic effector cells is tested following in vitro incubation of lymphocytes with i-RNA, after which the cytotoxic activity of the treated lymphocytes is tested against cultured human tumor cells of the same histological type as those used to immunize the Is-RNA donor sheep.

The lymphoblastoid cell line LDV/7 is induced with Is-RNA as follows:

1 mg of Is-RNA is dissolved in 0.5 ml RPMI 1640 medium: this solution is made 0.35 M with respect to sucrose. $10^7$ LDV/7 cells are subsequently suspended in this solution and incubated for at least 30 minutes at 37° C. with continuous stirring. At the end of the incubation, fresh medium is added and the final volume is adjusted to 20 ml, thus bringing the cell concentration to $5 \times 10^5$ cells/ml. Since the mean doubling time of this cell line, when cultured under static conditions, is of the order of 24 hours, a volume of fresh medium (RPMI 1640, supplemented with 10% foetal calf serum), equal to the existing volume of the culture, is added every day, until the total volume of the culture reaches 3 liters, thus yielding approximately $2 \times 10^9$ cells. An aliquot of $10^7$ cells from this culture is induced a second time with the same Is-RNA following the same procedure. This newly induced aliquot serves for the seeding of a second culture which again is supplemented with fresh medium and grown until a desired number of cells is obtained. Usually the second culture is grown to provide $4 \times 10^9$ cells. The cells from the two cultures are pooled and stored frozen at $-20°$ C. I-RNA is extracted from the frozen cells (Ic-RNA) and assayed for biologic activity as described above. Between 0.7 and 1.5 mg of total RNA are usually obtained from $10^9$ cells. All batches of Ic-RNA extracted in this manner gave a non-degraded profile on sucrose density gradients.

The Ic-RNA's extracted from the cultured LDV/7 cells are tested for their ability to induce naive human lymphocytes to become cytotoxic to tumor target cells in vitro. The human lymphocytes were isolated from the peripheral blood of a healthy donor on Ficoll-isopaque gradients. Their activity is compared to that of the inducing Is-RNA preparations. In eight out of ten experiments it was shown that Ic-RNA preparations were capable of conferring significant cytotoxicity for tumor target cells to naive allogeneic lymphocytes. Table 1 shows results from two typical successful experiments.

Allogeneic human lymphocytes from the peripheral blood of a healthy blood donor were used as effector cells. $5 \times 10^7$ cells were incubated with i-RNA extracted from (a) uninduced LDV/7 cells (c-RNA), (b) a sheep immunized with KLH (Is-RNAk), (c) a sheep immunized with human colon carcinoma cells (Is-RNAc), (d) a sheep immunized with human melanoma cells (Is-RNAm) and (e) three batches of LDV/7 cells (Ic-RNA), after induction with each of the three different types of Is-RNA (k, c and m). Lymphocytes incubated with no i-RNA provided the control (C1). Each figure represents the mean of six values. Significant differences ($P<0.005$) were observed between the activity of the I-RNA's obtained either from the sheep immunized with tumor cells, or from LDV/7 cultures induced with these anti-tumor Is-RNA's, on the one hand, and the controls (lymphocytes incubated with no RNA, c-RNA, Is-RNAk or Ic-RNAk), on the other. No significant differences were seen between the cytotoxicity indices obtained with active Is-RNA preparations and the Ic-RNA's from LDV/7 cells induced with these Is-RNA's. NT=not tested.

"Allogeneic-lymphocytes" is used herein reference to the patient, donor of the tumor cells employed for sheep immunization. The cultured tumor cells used for the cytotoxicity tests were allogeneic with respect to the tumor cell donor and were of the same histological type as those used for the sheep immunization. The same blood donor provided the effector lymphocytes throughout these experiments.

Table 1

|         | 1           | 2           |
|---------|-------------|-------------|
| C1      | 0 ± 0.07    | 0 ± 0.10    |
| c-RNA   | 0.03 ± 0.05 | 0.07 ± 0.05 |
| Is-RNAk | NT          | 0.12 ± 0.02 |
| Ic-RNAk | NT          | 0.10 ± 0.03 |
| Is-RNAc | 0.50 ± 0.06 | 0.38 ± 0.09 |
| Ic-RNAc | 0.48 ± 0.06 | 0.30 ± 0.08 |
| Is-RNAm | 0.34 ± 0.03 | 0.33 ± 0.08 |
| Ic-RNAm | 0.34 ± 0.03 | 0.23 ± 0.05 |

However, it must be emphasized that these results do not suggest that the observed cytotoxicity is solely due to tumor specificities, since both the Is-RNA and the Ic-RNA preparations may be transferring immune reactivity against HL-A specificities as well as against tumor associated antigens. What is clearly shown is that Ic-RNA confers similar cytotoxicity indices to human normal lymphocytes as these conferred by the Is-RNA used for the induction.

It should also be noted that the LDV/7 cells are capable of producing Ic-RNA carrying the same specificities as the Is-RNA at least 10 weeks after the initial induction, and Ic-RNA showed the same specific activity whenever it was extracted 3–10 weeks after the induction.

EXAMPLE 4

I-RNA is extracted from the lymphoid tissues of sheep immunized either with Keyhole Limpet Haemocyanin (KLH); or with human tumor tissues (melanoma, colon carcinoma), KLH and Freund's Complete Adjuvant (FCA); or with FCA alone. I-RNA from non-immunized sheep is extracted under the same conditions. A hot phenol method is used for RNA extraction. The DNA, RNA and protein concentration of each preparation are determined and absence of significant degradation determined by analysis of sucrose density gradient profiles. The I-RNA preparations are kept lyophilized until use.

The LDV/7 lymphoblastoid cell line was used for these experiments. The cells grow in RPMI 1640 medium (Gibco), supplemented with 10% foetal calf serum (FCS), in suspension culture and their average doubling time, under the present experimental conditions, is approximately 24 hours.

For induction $10^7$ LDV/7 cells are incubated for 60 minutes in 1 ml of RPMI 1640 medium, without FCS, containing 1 mg of I-RNA. At the end of the incubation period, 19 ml of medium with 10% FCS is added, so that the cell concentration is adjusted to $5.10^5$ cell/ml. The cells are then grown under standard culture conditions.

Evidence for the formation of membrane receptors, specific for the given antigen, on the surface of the induced LDV/7 cells:

(a) Immune cytoadherence

Sheep red blood cells (SRBC) are mixed with an equal volume of a 0.005% tannic acid solution and incubated for 10 minutes at 37° C. After washing in phosphate buffered saline (PBS), the cells are suspended in PBS at a 1:20 ratio volume per volume. 1 ml of this suspension is mixed with 5 ml of PBS containing 1 mg/ml of KLH and incubated for 10 minutes at 37° C., in order to fix the antigen on the SRBC membranes. After washing, the antigen coated SRBC are resuspended in 5 ml of PBS. Washed LDV/7 cells are mixed with antigen coated SRBC and incubated for two hours at 37° C. Samples are taken at the end of the incubation period, placed between glass slides and cover slips, and counted under the microscope. LDV/7 cells to which more than 3 SRBC are attached are considered as "rosetting" cells.

LDV/7 cells, induced with I-RNA from sheep immunized with KLH, show a significantly higher number of rosetting cells, when they are incubated with KLH, than do cells induced with RNA obtained from non-immunized animals, or with I-RNA from sheep immunized with an antigen different than the one used for coating the SRBC e.g. FCA. The average number of rosetting cells observed for an induced culture is of the order of 10%.

(b) Immunofluorescence

KLH labelled with tetramethyl rhodamine isothiocyanate, isomer G (Sigma) (RITC) is used to localize the KLH membrane receptors by direct immunofluorescence. 200 μg/ml of RITC labelled KLH is incubated with $6.10^5$ LDV/7 cells for 30 minutes.

Cells are incubated under the same conditions with non labelled KLH. The latter is revealed on the cell surface by a rabbit anti-KLH antiserum conjugated to fluorescein isothiocyanate, isomer I (Sigma) (FITC). Rabbit anti-KLH antisera are prepared by three biweekly injections of 1 mg of KLH.

A Goat anti-rabbit FITC-labelled antiserum is used in the indirect technique to develop unlabelled rabit anti-KLH antibodies fixed on the surface of LDV/7 cells incubated with KLH.

LDV/7 cells induced with sheep i-RNA-KLH and incubated with KLH show fluorescent staining in the direct (using labelled KLH) or the indirect (using fluorescent rabbit anti-KLH antiserum or unlabelled rabbit anti-KLH antiserum and a fluorescent goat anti-rabbit antiserum) test. (see Table 2). Cells induced with sheep i-RNA-FCA, or i-RNA from non-immunized sheep, do not show antigen receptors for KLH on their surface, thus remaining non-fluorescent. Specific immune blocking (IB) confirmed the specificity of the staining. Approximately 30% of the cells from the induced cultures were found to be fluorescent.

Table 2

|  | Non-induced cells | i-RNA-KLH induced cells |
|---|---|---|
| Direct staining with RITC labelled KLH | — | + |
| I.B.: pre-incubation with KLH followed by RITC labelled KLH | — | — |
| Indirect staining: incubation with KLH followed by FITC labelled rabbit anti-KLH antiserum | — | ++ |
| I.B.: pre-incubation with KLH, then unlabelled rabbit anti-KLH antiserum, followed by FITC labelled rabbit anti-KLH antiserum | — | — |
| Indirect staining: incubation with KLH followed by rabbit anti-KLH antiserum and then followed by an FITC labelled goat anti-rabbit γ-globulin anti-serum | — | +++ |

The degree of fluorescent staining is expressed as the percentage of fluorescing cells as follows:
+ >30%
++ >40%
+++ >50%
FITC Fluorescein isothiocyanate Isomer I
RITC Tetramethyl rhodamine isothiocyanate Isomer G.

(c) Peroxidase-diaminobenzidine (PO-DAB):

See Graham, R. C. and Karnovsky, M. J.:

The early stages of absorption of injected horseradish peroxidase in the proximal tubules of mouse kidney: ultrastructural cytochemistry by a new technique. J. Histochem. Cytochem., 14, 291, 1966.

$10^6$ LDV/7 cells, incubated with 1 ml of a solution of KLH (200 μg/ml), after thorough washing, are fixed with Karnovsky fixative for 5 minutes and afterwards exposed to a rabbit anti-KLH antiserum. After further thorough washing, the cells are exposed to a goat anti-rabbit antiserum conjugated with horseradish peroxidase (Institut Pasteur). The preparation is exposed to a saturated solution of 3-3'diamino-benzidine base free (DAB) (Sigma) for 15 minutes at 20° C., and then fixed in Karnovsky fixative for 30 minutes. The pellet is then dehydrated and embedded in Epon 812. Thin sections are obtained using a Reichert microtome and examined unstained or lead contrasted in a Philips 300 electron microscope.

i-RNA-KLH induced cells, incubated with KLH, and stained with PO-DAB show, in electron microscopy, a thick dark line on the outer surface of their membranes, corresponding to the peroxidase reaction, and thus showing the KLH fixation on the membrane antigen receptors. Approximately 30% of the KLH-I-RNA cells were found to be peroxidase positive.

It therefore is concluded that this i-RNA (of sheep origin) transfers information to xenogeneic lymphoblastoid cells in culture. The latter are capable of re-expressing this information. The results show that xenogeneic I-RNA is not just passively incorporated and replicated by the LDV/7 lymphoblastoid cells, but becomes functional in that its information is expressed as soon as it is incorporated in the host cell. Indeed, it induces cell surface changes, the appearance of specific antigen receptors, and furthermore, the secretion of specific γ-globulins, though this latter point is not demonstrated in this Example.

EXAMPLE 5

I-RNA is extracted in the usual way from the lymphoid tissues of rabbits immunised with brucella bacteria. The i-RNA preparations thus obtained were used to induce the LDV/7 cell line using the techniques described in Example 3. The supernatant liquid obtained from the culture medium was analysed for the presence of gamma-globulins specific to the brucella bacteria which was used as the original sensitizing antigen. The presence of such specific gamma-globulins was indicated by immunofluorescence techniques, and by agglutination when samples of the supernatant liquid were combined with brucella bacteria.

EXAMPLE 6

Following the method of Example 5, gamma-globulins specific to coccidioidin were raised using the LDV/7 cell line. The i-RNA used to induce the cell culture system was obtained from the lymphoid tissues of rabbits which had previously been sensitized to coccidioidin.

We claim:

1. A process for the production of gamma-globulins specific to a given antigen, which process comprises culturing an inducible established cell line of lymphoid origin, which spontaneously produces gamma-globulins, in vitro in the presence of material which is specific to said given antigen and which is selected from:
   (a) immune nucleic acids obtained from the lymphoid cells of donors sensitised to said given antigen, said donors being selected from humans and animals,
   (b) immune nucleic acids obtained from cells of an established cell line culture sensitised to said given antigen by having been cultured with immune nucleic acids or immune dialysates specific to said given antigen,
   (c) immune dialysates obtained from the lymphoid cells of donors sensitised to said given antigen, said donors being selected from humans and animals,
   (d) immune dialysates obtained from cells of an established cell line culture sensitised to said given antigen by having been cultured with immune nucleic acids or immune dialysates specific to said given antigen, or
   (e) the liquid phase of an established cell line culture sensitised to said given antigen by having been cultured with immune nucleic acids or immune dialysates specific to said antigen.

2. A process according to claim 1 wherein said inducible established cell line is a myeloma cell line.

3. A process according to claim 1 wherein said inducible established cell line is a lymphoblastoid cell line.

4. A process according to claim 1 wherein said inducible established cell line is selected from the group consisting of the LDV/7 cell line, the BRI 8 cell line and the BEC/11 cell line.

5. A process according to claim 1 wherein said material (a) is i-RNA obtained from the lymphoid cells of a sensitised animal donor.

6. A process according to claim 5 wherein the animal is selected from a sheep, rabbit, guinea pig and rat.

7. A process according to claim 1 wherein said material (b) is i-RNA obtained from the cells of a LDV/7 culture sensitised to said given antigen.

8. A process according to claim 1 wherein said material (d) is obtained from cells of a LDV/7 culture sensitised to said given antigen.

9. A process according to claim 1 wherein said given antigen is selected from Keyhole-limpet haemocyanin, coccidioidin, histoplasmin, brucella bacteria, melanoma cells and colon carcinoma cells.

10. A process according to claim 1 which further comprises cloning the resulting established cell line of lymphoid origin which is spontaneously producing gamma-globulins specific to said given antigen.

11. A process for the production of immune nucleic acids and immune dialysates, both specific to a given antigen, which process comprises culturing an inducible established cell line of lymphoid origin, which spontaneously produces gamma-globulins, in vitro in the presence of material which is specific to said antigen and which is selected from:
(a) immune nucleic acids obtained from the lymphoid cells of donors sensitised to said given antigen, said donors being selected from humans and animals,
(b) immune nucleic acids obtained from cells of an established cell line culture sensitised to said given antigen by having been cultured with immune nucleic acids or immune dialysates specific to said given antigen, or
(c) the liquid phase of an established cell line culture sensitised to said given antigen by having been cultured with immune nucleic acids or immune dialysates specific to said antigen, or in the case of the production of immune nucleic acids, also from:
(d) immune dialysates obtained from the lymphoid cells of donors sensitised to said given antigen, said donors being selected from humans and animals, or
(e) immune dialysates obtained from cells of an established cell line culture sensitised to said given antigen by having been cultured with immune nucleic acids or immune dialysates specific to said given antigen.

12. A process according to claim 11 wherein said inducible established cell line is a myeloma cell line.

13. A process according to claim 11 wherein said inducible established cell line is a lymphoblastoid cell line.

14. A process according to claim 11 wherein said inducible established cell line is selected from the group consisting of the LDV/7 cell line, the BRI/8 cell line and the BEC/11 cell line.

15. A process according to claim 11 wherein said material (a) is i-RNA obtained from the lymphoid cells of a sensitised animal donor.

16. A process according to claim 15 wherein the animal is selected from a sheep, rabbit, guinea pig and rat.

17. A process according to claim 11 wherein said material (b) is i-RNA obtained from the cells of a LDV/7 culture sensitised to said given antigen.

18. A process according to claim 11 wherein said material (e) is obtained from cells of a LDV/7 culture sensitised to said given antigen.

19. A process according to claim 11 wherein said given antigen is selected from Keyhole-limpet haemocyanin, coccidioidin, histoplasmin, brucella bacteria, melanoma cells and colon carcinoma cells.

* * * * *